(12) United States Patent
Yoshimura et al.

(10) Patent No.: US 6,283,596 B1
(45) Date of Patent: Sep. 4, 2001

(54) SLIT-LAMP BIOMICROSCOPE

(75) Inventors: Kazuhiro Yoshimura; Yasuhisa Murakami, both of Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/629,461

(22) Filed: Jul. 31, 2000

(30) Foreign Application Priority Data

Jul. 30, 1999 (JP) .................................................. 11-216416
Jul. 30, 1999 (JP) .................................................. 11-216418

(51) Int. Cl.[7] ...................................................... A61B 3/10
(52) U.S. Cl. ............................................................. 351/214
(58) Field of Search ................................... 351/205, 208, 351/213, 214, 215, 221, 206; 600/310, 558

(56) References Cited

U.S. PATENT DOCUMENTS 3,830,562 * 8/1974 McGrann et al. .................... 351/214
5,530,493 * 6/1996 Suzuki .................................. 351/206
5,801,807 * 9/1998 Satake et al. ........................ 351/221

FOREIGN PATENT DOCUMENTS 56-72842   6/1981 (JP) .
60-114233  6/1985 (JP) .
10-33481   2/1998 (JP) .

* cited by examiner

*Primary Examiner*—George Manuel
(74) *Attorney, Agent, or Firm*—Finnegan, Henderson, Farabow, Garrett & Dunner, L.L.P.

(57) ABSTRACT

A slit-lamp biomicroscope which illuminates an eye to be examined with slit illumination light, the biomicroscope comprises an illumination optical system provided with an illumination light source and a slit plate of which slit width is adjustable, a plurality of types of filters each having a different optical characteristic which are inserted into, and removed from an optical path of the illumination optical system, a filter detection device for detecting a type of the filter being inserted in the optical path of the illumination optical system, a light amount change device for changing an amount of illumination light on a side of the illumination light source with respect to the slit plate and a control device for controlling the light amount change device such that the amount of illumination light is adjusted to an amount corresponding to the detected filter based on a detection result obtained by the filter detection device.

17 Claims, 4 Drawing Sheets

SLIT-LAMP BIOMICROSCOPE

BACKGROUND OF THE INVENTION

1. Field of the Invention

The present invention relates to a slit-lamp biomicroscope for observing (examining) an eye to be examined by illuminating the eye with slit light.

2. Description of Related Art

Observations of an eye to be examined (a patient's eye) using a slit-lamp biomicroscope have been widely used as general examinations in ophthalmology. Normally, a slit-lamp biomicroscope is adjustable in its slit width of illumination light for illuminating the eye to an intended width in accordance with aims of observations.

In addition, some slit-lamp biomicroscopes comprise a plurality of filters inside thereof for changing a color of light or for changing quality of light in order to suppress heat that the illumination light generates. This type of slit-lamp biomicroscope is also capable of selectively inserting an intended filter into an illumination optical path in accordance with aims of observations.

However, in general, as the slit width is made narrower, the illumination light amount decreases, and therefore, the illumination light amount needs to be increased to make up for the light loss. In addition, the illumination light amount decreases when passing through the filters. Because of this light loss, when adjusting the slit width or changing over the filters, an examiner (operator) is required to operate an illumination light adjustment knob or the like in order to adjust the illumination light amount based on his experience. This operation imposes a burden on the examiner and, if it takes long for the adjustment, examination efficiency decreases.

When using the slit light biomicroscope, an examinee's head is supported by a headrest having a chin rest and a forehead rest so that the examinee's head is not allowed to move. Thereafter, the examiner operates a knob or the like to move the chin rest up and down thereby to bring the eye into a predetermined position.

Once the eye is properly positioned, the main body of the biomicroscope is moved as necessary to observe the eye: The microscope comprises two units which are an illumination unit provided with an illumination optical system for emitting the illumination light onto the eye and a microscope unit (observation unit) provided with an eyepiece portion as well as an observation optical system for observing the eye. In the case of observing a cross-sectional image of the eye, the slit width is made narrow. By adjusting an axial angle between an illumination optical axis of the illumination optical system and an observation optical axis of the observation optical system, a cross-sectional image of a cornea, an anterior chamber, a crystalline lens, a vitreous body or other portions of the eye can be observed. However, the knob for moving the chin rest up and down is normally provided near the chin rest, and therefore, the examiner is required to extend his arm to reach the knob every time he operates the knob. Apparently, this is extremely inconvenient.

In addition, in order to observe a cross-sectional image of the eye, the observation optical axis needs to be shifted to right or left to some extent instead of being positioned in the front of the eye. As the result of this shift, the eyepiece portion of the microscope unit is as well shifted to right or left to some extent so that the examiner is forced to observe the eye in uncomfortable posture.

SUMMARY OF THE INVENTION

The present invention has been made in view of the above circumstances and has an object to overcome the above problems and to provide a slit-lamp biomicroscope which does not require adjustment of the illumination light amount every time the slit width is adjusted or the filter is changed over and therefore is operated without much trouble.

Another object of the present invention is to provide a slit-lamp biomicroscope with witch an examiner can make alignment of the eye or observe the eye without taking uncomfortable posture.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a slit-lamp biomicroscope which illuminates an eye to be examined with slit illumination light, the biomicroscope comprises an illumination optical system provided with an illumination light source and a slit plate of which slit width is adjustable, a plurality of types of filters each having a different optical characteristic which are inserted into, and removed from an optical path of the illumination optical system, filter detection means for detecting a type of the filter being inserted in the optical path of the illumination optical system, light amount change means for changing an amount of illumination light on a side of the illumination light source with respect to the slit plate; and control means for controlling the light amount change means such that the amount of illumination light is adjusted to an amount corresponding to the detected filter based on a detection result obtained by the filter detection means.

In another aspect of the present invention, a slit-lamp biomicroscope which illuminates an eye to be examined with slit illumination light, the biomicroscope comprises an illumination optical system provided with an illumination light source and a slit plate of which slit width is adjustable, a plurality of types of filters each having a different optical characteristic which are inserted into, and removed from an optical path of the illumination optical system, filter detection means for detecting a type of the filter being inserted in the optical path of the illumination optical system, slit width detection means for detecting the slit width, a photoelectric photographic optical system for photographing the eye, the photoelectric optical system also functions as an observation optical system, a display for displaying a photographed image of the eye as well as information about the detected slit width and the amount of illumination light, light amount change means for changing an amount of illumination light on a side of the illumination light source with respect to the slit plate, and control means for controlling the light amount change means such that the amount of illumination light is adjusted to an amount corresponding to the detected filter based on a detection result obtained by the filter detection means.

Further, in another aspect of the present invention, a slit-lamp biomicroscope which illuminates an eye to be examined with slit illumination light, the biomicroscope comprises an illumination optical system provided with an illumination light source and a slit plate of which slit width is adjustable, slit width detection means for detecting the slit width, light amount change means for changing a amount of illumination light on a side of the illumination light source with respect to the slit plate, and control means for controlling the light amount change means such that the amount of illumination light is adjusted to an amount corresponding to the detected slit width based on a detection result obtained by the slit width detection means.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of a slit-lamp biomicroscope embodying the present invention will now be given referring to the accompanying drawings.

Overall Configuration

Figure 1A:
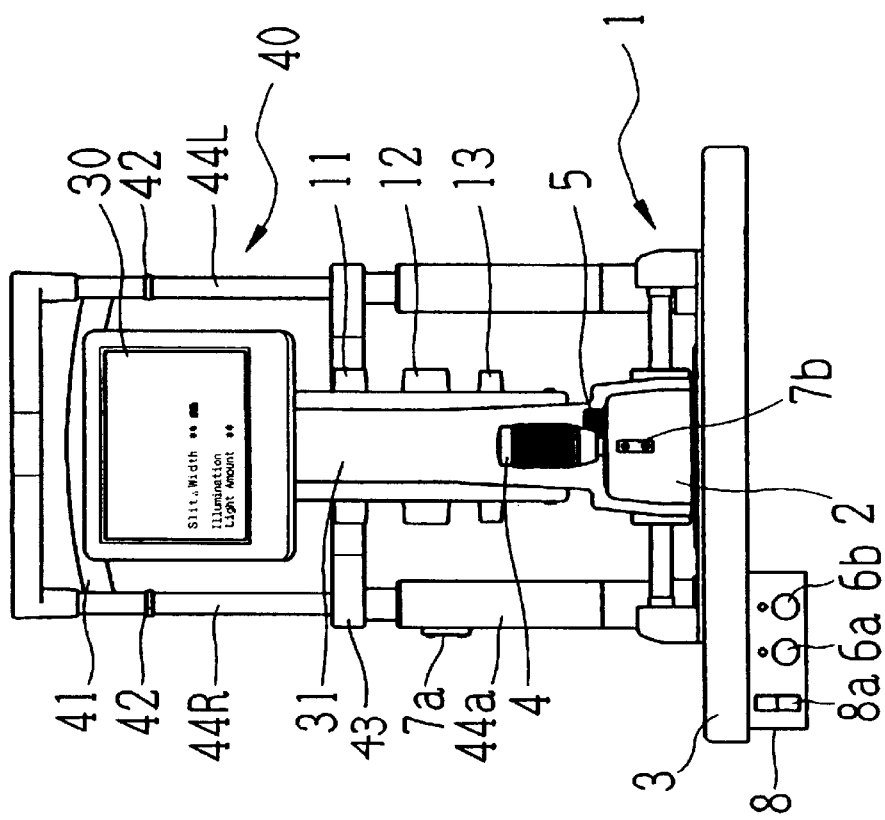
FIGS. 1A and 1B are views showing external representations of a slit-lamp biomicroscope consistent with one preferred embodiment of the present invention.
Figure 1B:
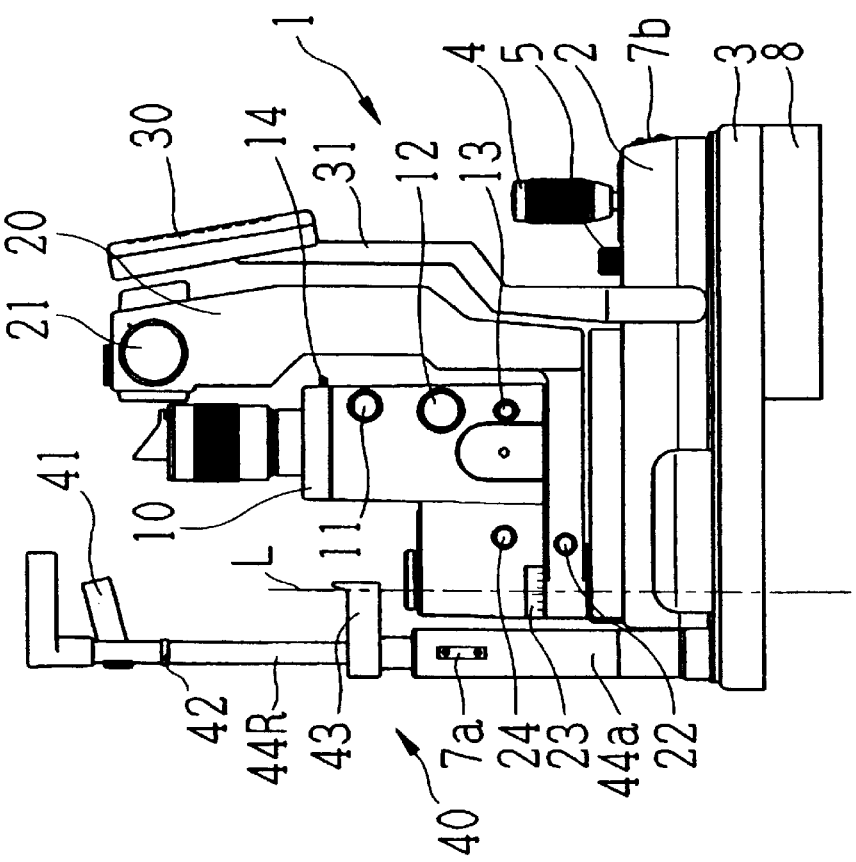

FIG. 1A is a side view showing an external representation of the slit-lamp biomicroscope and FIG. 1B is a view showing an external representation of the slit-lamp biomicroscope seen from an examiner's (operator's) side.

The slit-lamp biomicroscope 1 comprises a base 2 at the bottom thereof. The base 2 is slidable along a table 3 in a horizontal direction by a known moving mechanism so that the base 2 may be moved coarsely and finely on the table 3 by operating a joystick 4. Mounted to the table 3 is a head rest 40 for fixedly holding an examinee's (patient's) head (of which details will be described later).

Reference numeral 10 denotes an illumination unit for emitting slit illumination light onto an eye to be examined (patient's eye) and an illumination optical system (described later) is disposed therein. The illumination unit 10 is rotatable on an axis L relative to the base 2 so that the examiner can change an illumination angle of the illumination light arbitrarily (can shift an illumination optical axis of the illumination optical system).

Reference numeral 20 denotes an observation unit for observing the eye comprising inside thereof an observation optical system (described later) provided with a CCD camera 58 and the like. Similarly to the illumination unit 10, the observation unit 20 is rotatable on the axis L so that the examiner can change an observation angle arbitrarily (can shift an observation optical axis of the observation optical system).

A position (rotational position) of the observation unit 20 relative to the base 2 can be fixed using a fixation knob 22. In addition, a position (rotational position) of the illumination unit 10 relative to the observation unit 20 can be fixed using a fixation knob 24. The state of openness relatively between the illumination unit 10 and the observation unit 20 (an open angle between the illumination optical axis and the observation optical axis) is indicated by an axial angle calibration 23.

Reference numeral 30 denotes a display for displaying an image photographed by the camera 58. The display 30 is fixed to the base 2 by way of a supporting shaft 31. In the case of the biomicroscope 1 of the present embodiment, there is no eyepiece portion comprising eyepiece lenses, and the examiner observes the image of the eye displayed on the display 30. As shown in FIG. 1B, information such as parameters for various condition setting are also displayed on the display 30.

Reference numeral 8 denotes a control box provided with a power switch 8a, a slit-based light amount setting switch 6a, and a filter-based light amount setting switch 6b: The switch 6a is for setting the illumination light amount in accordance with the slit width and the switch 6b is for setting the illumination light amount in accordance with each type of the filters (which will be described later) disposed in the illumination unit 10. In addition, provided on the base 2 adjacent to the joystick 4 is a light adjusting knob 5 for adjusting the illumination light amount.

Configuration of Important Units

Figure 2:
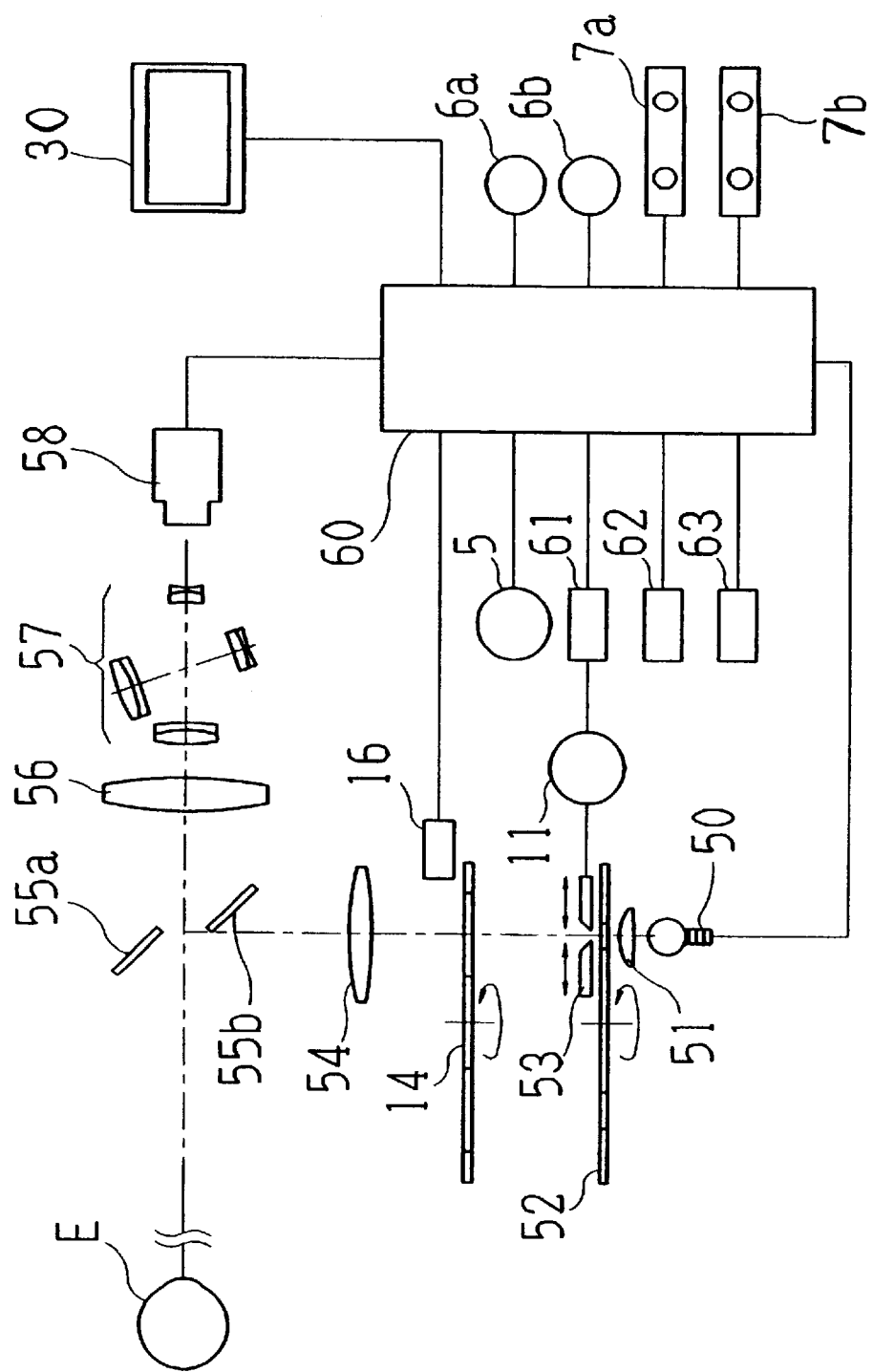
FIG. 2 is a view showing a schematic configuration of an optical system and a control system of the biomicroscope consistent with the present invention.
Figure 3:
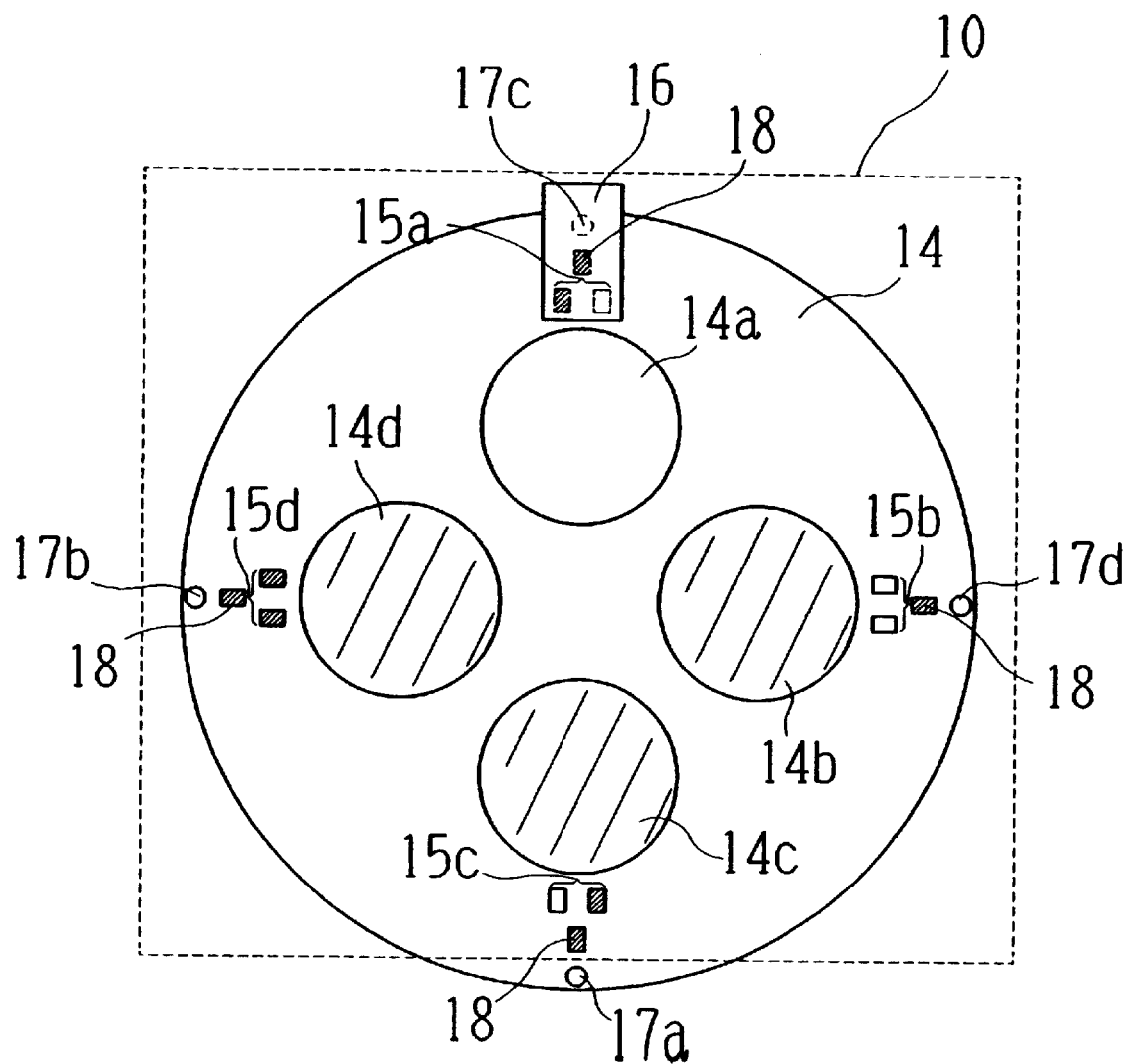
FIG. 3 is a view showing a schematic configuration of a filter disk consistent with the present invention.
Figure 4:
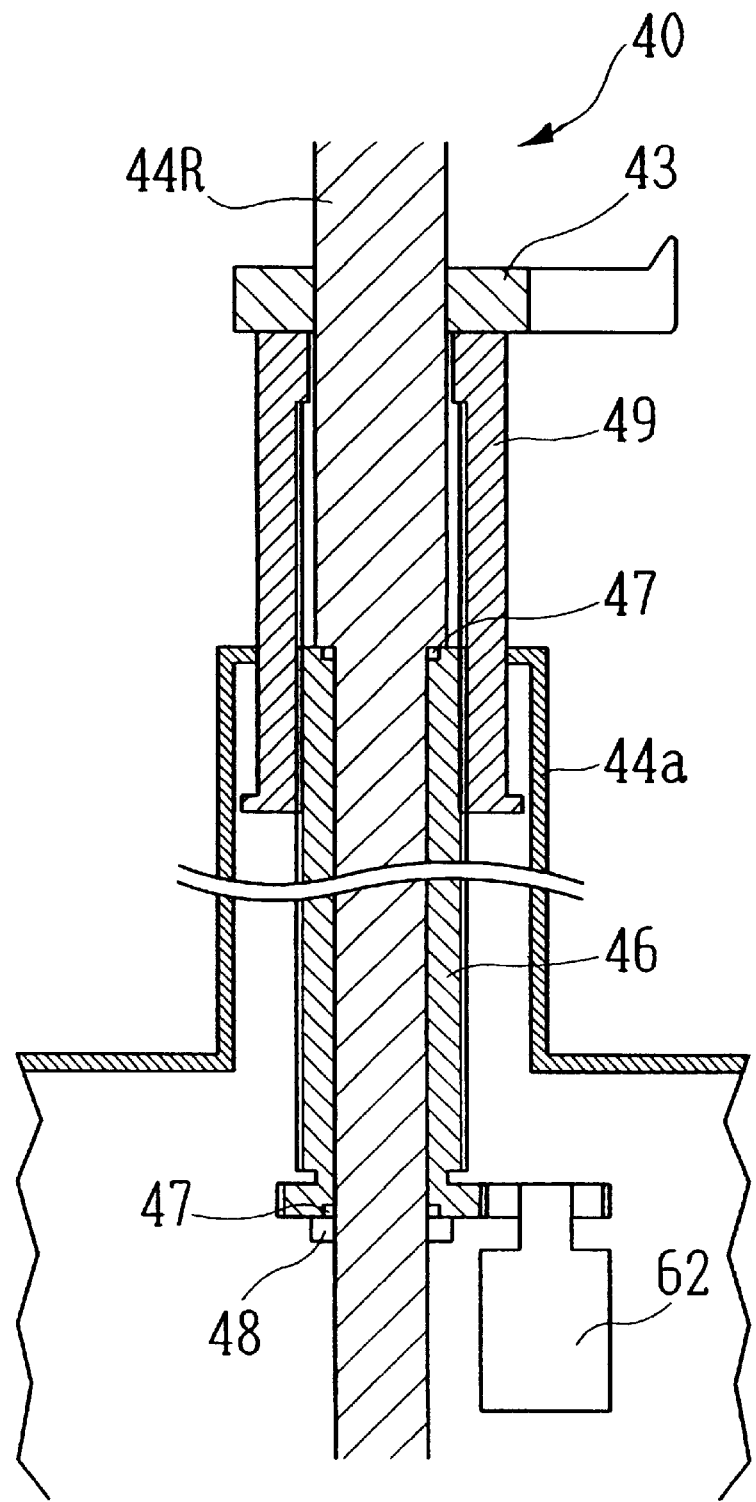
FIG. 4 is a sectional view showing a schematic configuration of an up and down movement mechanism of a chin rest consistent with the present invention.

Hereinafter, description is given separately to configuration of each unit, namely the illumination unit 10, the observation unit 20 and the head rest 40 with reference to FIGS. 1–4. FIG. 2 is a view showing a schematic configuration of the optical system and the control system provided inside the biomicroscope 1. FIG. 3 is a view showing a schematic configuration of a filter disk comprised in the illumination unit 10. FIG. 4 is a sectional view showing a schematic configuration of an up and down moving mechanism for a chin rest 43 comprised in the head rest 40.

A. Illumination Unit

Provided inside the illumination unit 10 is the illumination optical system comprising an illumination light source 50, a condenser lens 51, an aperture 52, a variable slit plate 53, the filter disk 14, a projection lens 54 and dividing mirrors 55a and 55b (see FIG. 2). Visible light emitted from the light source 50 passes through the lens 51 and is determined its height and width by the aperture 52 and the slit plate 53 respectively so that the light is formed into a slit shape. Thereafter, the illumination light passes through the filter disk 14 and the lens 54 and is reflected by the mirrors 55a and 55b so as to illuminate an eye E to be examined. In the case of observing a fundus of the eye E, both illumination and observation are carried with the aid of a contact lens.

The aperture 52 is constituted by a circular plate having a plurality of openings in different diameters ranging from 0.2 mm to 14 mm along a circumference thereof. By rotating an aperture changeover knob 13 (see FIG. 1), one of the openings having a different diameter is positioned on the illumination optical axis one by one so that the diameter (height) of the illumination light can be changed in a stepwise fashion.

The slit plate 53 is constituted by two blades and these blades are coupled to a slit adjusting knob 11 via a plurality of not-illustrated cams and the like. Rotation of the knob 11 causes the blades to open or close. Therefore, the slit width can be changed in a continuous fashion. Here, the slit width can be adjusted continuously within a range between 0–14 mm. The knob 11 is provided with a potentiometer 61. A control unit 60 can obtain the slit width from a rotation amount of the knob 11 that is detected by the potentiometer 61. In addition, the slit can be inclined by operating a slit rotating knob 12.

The filter disk 14 is configured to be exposed partly to the outside of a casing of the illumination unit 10 (see FIG. 3). By rotating the exposed part, any intended filter can be placed in turn on the illumination optical axis (in the optical path). In addition, through rotating the filter disk 14, a tactile feel of click is given at about every 90 degrees by a not-illustrated click mechanism to indicate that one of the filters is properly inserted into the optical path.

There are a transparent portion 14a, a heat wave absorbing filter 14b having antiglare and antiheat effects, a red free filter 14c used for, for example, examining anomaly in optic nerve fibers, and a blue filter 14d used for observing fluorescein staining reaction provided on the filter disk 14 at 90 degrees intervals. Adjacent to the transparent portion 14a and each of the filters 14b–14d, identification tags 15a–15d are provided respectively for identifying the type of the filters (or the transparent portion) being inserted. Also, an identification tag 18 is provided adjacent to each of the transparent portion 14a and the filters 14b–14d for detecting whether the filter is properly inserted. The identification tags 15a–15d are constituted from two types of plates, one reflects light and one does not, in combination. By varying the combination, the transparent portion 14a and each of the filters 14b–14d being inserted in the illumination optical axis are identified. The identification tags 15a -15d are identified by a photointerrupter 16. The control unit 60 detects which type of the filter is being inserted in the illumination optical axis based on output signals from the photointerrupter 16. On the other hand, each of the identification tags 18 comprises only a reflecting plate and is used to indicate that one of the transparent portion 14a and the filters 14b–14d is being inserted. Detection of the identification tags 18 is also performed by the photointerrupter 16.

Reference numerals 17a–17d denote marks to visually indicate the type of the filters being inserted into the illumination optical axis. Each mark is color-coded to indicate the type of the filter. Specifically, the mark 17a (white) corresponds to the transparent portion 14a, the mark 17b (red) corresponds to the filter 14b, the mark 17c (green) corresponds to the filter 14c, and the mark 17d (blue) corresponds to the filter 14d. Each of those marks 17a–17d is provided adjacent to the filter positioned opposite to the corresponding filter. For example, when the transparent part 14a is being inserted into the illumination optical axis, the mark 17a appears outside the illumination unit 10 so that the examiner can see the type of the filter being inserted at a glance.

B. Observation Unit

Disposed inside the observation unit 20 is the observation optical system comprising an objective lens 56, a variable power lens 57 and the CCD camera 58 (see FIG. 2). Since the illumination light from the illumination unit 10 is divided by the dividing mirrors 55a and 55b, there is no obstruction to the photography along the optical axis so that reflected light from the eye E can be received by the camera 58. An image photographed by the camera 58 is displayed on the display 30 via the control unit 60. 21 is a magnification changeover knob (see FIG. 1), which is used for changingover the lens 57 so as to change an observation magnification of the display 30.

C. Head Rest

Between two poles 44R and 44L which are fixedly mounted to the table 3, a forehead rest 41 and the chin rest 43 are provided to firmly hold the examinee's head (see FIG. 1). The pole 44R is covered its lower part with a pole cover 44a, and a mechanism for moving the chin rest 43 up and down electrically is provided inside the cover 44a. The up and down movement of the chin rest 43 is activated by a switch 7a provided on the side of the cover 44a and also by a switch 7b provided on the base 2. 42 is an eye level marker provided to each of the poles 44R and 44L for adjusting a vertical position of the eye E.

Detailed description is now given to the up and down movement mechanism of the chin rest 43 (see FIG. 4). A feed screw portion 46 is inserted through a gap between the pole 44R and the cover 44a, and the screw portion 46 is rotatably held to the pole 44 by a bearing 47. The screw portion 46 is also fixed by a stopper 48 so as to prevent up and down movement thereof. Further, a gear portion formed at the lower end of the screw portion 46 is in mesh with a gear provided to a motor 62. 49 is an up and down nut portion through which the pole 44R is inserted, and which is in helical engagement with the screw portion 46. The chin rest 43 is fixedly mounted to the upper end of the up and down nut portion 49. Due to this configuration, rotation of the motor 62 causes the screw portion 46 to rotate. By the rotation movement of the screw portion 46, the nut portion 49 which is in helical engagement with the screw portion 46 is fed into up and down directions, and hence the chin rest 43 can be moved in up and down directions in a nonstepwise fashion.

Next, description is given to use of the biomicroscope having the configuration described above. First, description is given to how to adjust the illumination light amount in response to the adjustment of the slit width or to the changeover of the filter.

When the power is turned on using the switch 8a, the control unit 60 displays an image being captured by the camera 58 on the display 30. In order to make such a setting that the illumination light amount varies automatically in accordance with the slit width (the standard setting may be made prior to the shipment), the switch 6a and the like are operated preliminarily. At a push of the switch 6a, the control unit 60 lights an LED above the switch 6a to inform the examiner that preparation has been made for the slit-width-based adjustment of the illumination light amount. The control unit 60 also displays information about the current slit width as well as information about the illumination light amount on the display 30 (see FIG. 1B). Information about the illumination light amount may be displayed, for example, as a value representing the voltage of the light source 50 which is adjustable by the knob 5. Alternatively, the light received by the camera 58 may be displayed. While observing the information about the slit width being displayed on the display 30, the examiner operates the knob 11 to select the slit width of which illumination light amount the examiner intends to adjust (for example, the slit width may be made about 0.3 mm, which is a suitable slit width for observing a cross-sectional image of an anterior eye segment). Then, while observing the information about the illumination light amount being displayed on the display 30, the examiner operates the knob 5 until the illumination light amount reaches an amount which appears to be sufficient (when the slit width is made narrow, the illumination light amount is adjusted to the maximum level (for example about 50,000 lux)).

Once the illumination light amount corresponding to the selected slit width is determined, the examiner pushes the switch 6a once again to complete the setting. When the setting is completed (the switch 6a is pushed), the control unit 60 turns of f the LED and makes a memory 63 store the slit width and the illumination light amount at the time. The control unit 60 also dismisses the information about the slit width and the illumination light amount displayed on the display 30 and restores the display screen to its initial display screen for observation. The illumination light amount corresponding to the slit width is adjusted by the control unit 60 in a manner that the illumination light amount is made the predetermined amount (for example 50,000 lux) when the slit width is equal to a predetermined width or narrower (for example 0.3 mm or narrower).

In order to make such a setting that the illumination light amount is adjusted automatically in accordance with each filter that the filter disk 14 comprises, the switch 6b and the like are operated preliminarily. Similarly to the above case, the control unit 60 lights an LED above the switch 6b at the push of the switch 6b to inform the examiner that preparation has been made for the filter-type-based adjustment of the illumination light amount. The control unit 60 also displays the information about the type of the filter currently being inserted and information about the illumination light amount on the display 30. While observing the information about the type of the filter and the information about the illumination light amount being displayed on the display 30, the examiner operates the filter disk 14 to select the filter (to place the filter on the illumination optical axis) of which illumination light amount the examiner intends to set. Thereafter, the examiner operates the knob 5 so as to obtain an intended illumination light amount. For example, when the blue filter 14d is selected, the illumination light amount is attenuated so that the illumination light amount is set to the maximum level (for example about 50,000 lux).

Once the illumination light amount corresponding to the selected filter is determined, the examiner pushes the switch 6b once again to complete the setting. When the setting is completed (when the switch 6b is pushed), the control unit 60 turns off the LED and makes the memory 63 store the type of the filter and the illumination light amount at the time. The control unit 60 also restores the display screen of the display 30 to its initial state. Similarly, in the case where another setting is made such that the illumination light amount is automatically adjusted to another, the above operations are repeated.

Owing to the settings as described above, the optimum illumination light amount relative to the slit width or to each filter can be preliminarily set and stored in the memory by the examiner.

These settings may be made using a model eye. Also, since the information about the slit width, the type of the filter, and the illumination light amount is displayed on the display 30, it is possible that the examiner makes the settings based on his experience.

Next, description is given to operation for observing the eye E using the biomicroscope 1 of which illumination light amount has been already adjusted. First, the examinee's head is fixedly placed on the head rest 40. The examiner instructs the examinee to press his forehead against the forehead rest 41 and to place his chin on the chin rest 43. Thereafter, the chin rest 43 is moved up and down to adjust its height until the eye E (examinee's eye) comes to the same height as the eye level marker 42. The up and down movement of the chin rest 43 may be made by either of the switches 7a and 7b. Yet, when the examiner, who is on the side opposite from the examinee makes this adjustment by himself, the switch 7b mounted to the base 2 may be used. Since the switch 7b is located within his convenient reach, the examiner can make the adjustment efficiently without extending his arm to the side of the head rest 40.

On the other hand, in the case where an assistant such as a nurse makes the positional adjustment of the chin rest 43, the switch 7a may be used. The assistant may use the switch 7b mounted to the base 2 as well, but it raises the possibility that the assistant moves the biomicroscope 1 accidentally. To contrast, using the switch 7a mounted to the side of the head rest 40, the undesirable possibility is surely eliminated. In addition, the assistant is normally on the side of the examinee, and hence the switch 7a is more convenient to operate.

Once the positional adjustment of the eye E is completed, the examiner illuminates and observes the eye E. Referring to observation of the eye E, there are cross-sectional observation of an anterior eye segment, frontal observation of an anterior eye segment, observation of a fundus of the eye and the like. Hereinafter, description is briefly given to the cross-sectional observation of the anterior eye segment and the frontal observation of the anterior eye segment.

In the case of the cross-sectional observation of the anterior eye segment, it is required that the anterior eye segment be light-sectioned by the slit illumination light from the illumination unit 10 and that the cross section of the anterior eye segment be observed by the observation unit 20 (be photographed by the camera 58). The examiner first instructs the examinee to fix his gaze on a not-illustrated fixation light. Then, the examiner rotates the illumination unit 10 (the illumination optical axis) and the observation unit 20 (the observation optical axis) relatively on the rotation axis L to form an intended angle (for example about 25 degrees) between the illumination unit 10 and the observation unit 20 while observing the axial angle calibration 23. The angle between the two units may be fixed using the knob 22 or the knob 24.

In addition, in the case of the cross-sectional observation of the anterior eye segment, the slit width is set narrow using the knob 11. The condition of the slit width adjustment is detected by the potentiometer 61. If the control unit 60 confirms that the slit width is equal to, or less than the predetermined value stored in the memory 63 (for example 0.3 mm or less), the control unit 60 exerts controls so that the illumination light amount that the light source 50 emits is made equal to the predetermined illumination light amount (for example 50,000 lux). As the result, the examiner is not required to operate the knob 5. Instead, through adjustment of the slit width by operating the knob 11 alone, the intended (optimum) illumination light amount is achieved automatically, and therefore the examiner can go on to the next procedure efficiently. Here, in case where the examiner determines that the illumination light that has been adjusted automatically is not suitable, the examiner may operate the knob 5 to manually adjust the illumination light amount as in a conventional fashion. Operation signals issued in response to the operation of the knob 5 are inputted to the control unit 60, and whereby the control unit 60 temporarily releases the settings of the automatic adjustment of the illumination light and adjusts the illumination light.

Also, in the cross-sectional observation of the anterior eye segment, provided that the angle formed between the illumination unit 10 and the observation unit 20 is fixed using the knob 24, the cross-section may be taken at an intended angle by shifting the observation unit 20 on the axis L. As the result, the examiner can observe a cross-sectional image of the anterior eye segment taken at that angle on the display 30.

Here, it should be noted that in the case of a conventional biomicroscope with a microscope unit comprising an eyepiece portion, the eyepiece portion is made to shift as the microscope unit shifts on the axis L. As the result, the examiner is forced to make observation in uncomfortable posture or forced to take trouble to move his position before making observation. On the contrary, in the present embodiment, an image photographed by the camera 58 included in the observation unit 20 is displayed on the display screen 30 and therefore the examiner does not have to move: The examiner is able to observe the image from every angle while remain seated in front of the biomicroscope.

Next, description is given to the case of the frontal observation of the anterior eye segment. Here, description is specifically given to the case of fluorescein observation as one example. Prior to the observation, the examiner instills fluorescein on a corneal surface of the eye E, and then starts the frontal observation of the anterior eye segment after the expiration of a predetermined time period. In this observation, the slit width is made relatively wide so as to illuminate the entire cornea of the eye E with the illumination light. Next, the filter disk 14 is rotated to insert the blue filter 14d into the illumination optical axis. Once the blue filter 14d is placed on the illumination optical axis, the photointerrupter 16 detects that the blue filter 14d has been inserted and inputs detection signals to the control unit 60. When the detection signals are inputted, the control unit 60 controls the illumination light amount to the predetermined level (in this case, to the maximum level (for example 50,000 lux)). Generally, in the case of inserting the blue filter, the illumination light amount decreases drastically. Due to this decrease, it is conventionally required that the examiner operate the knob 5 to increase the illumination light amount. In the present embodiment, however, the illumination light amount is automatically adjusted, and therefore does not bother the examiner. This allows the examiner to concentrate on the observation and to carry out the examination smoothly.

The illumination light emitted from the light source 50 becomes blue light by the blue filter 14d and illuminates the entire cornea. In response, the corneal surface emits luminescence in specific color by fluorescein reaction. The examiner observes the corneal surface in such a state to measure a tear film breakup time and the like.

In addition, there is a case where the observation is made with the slit width changed while the filter remains unchanged. In the case where the slit width is changed by operating the knob 11 and where the slit width is determined to be equal to, or less than the predetermined value stored in the memory 63, the control unit 60 gives precedence to that predetermined value and adjusts the illumination light amount accordingly. The reason is that this is the case where the examiner considers observation with the changed slit width is important. In addition, although the illumination light amount is determined in accordance with the filter or the slit width, the illumination light amount may be adjusted arbitrarily by using the knob 5. The control unit 60 gives precedence to signals issued in response to the operation of the knob 5 and adjusts the illumination light amount in accordance with the operation signals.

In the preferred embodiment that has been described above, referring to the settings of the illumination light amount relative to the slit width or the filter, one setting of the illumination light amount is stored relative to each condition. Yet, it is possible that a plurality of settings may be stored instead of only one setting. This allows a plurality of examiners to make their own settings of the illumination light amount and to perform observation under the set illumination light amount of their own as necessary.

Further, the photointerrupter 16 is used to detect the changingover of the filter in the above embodiment, yet the photointerrupter is not an exhaustive example. For example, a potentiometer, an encoder or the like may be used to detect the rotation amount of the rotation disk 14 so as to detect the changingover of the filter. Further, in the case where a mechanism comprising a selection switch or the like to select each filter, and where the filter disk 14 is electrically rotated by using the selection switch, the changingover of the filter may be detected by detecting signals generated by the selection switch.

As described above, according to the present invention, the illumination light amount is preliminary set in accordance with the slit width or the type of the filter, and therefore it is not necessary that the examiner adjust illumination light amount upon observation thereby eliminating the burden imposed on the examiner. As the result, examinations can be performed efficiently and smoothly.

In addition, the examiner can perform observations without taking uncomfortable posture. That is, even when the observation unit is made to shift to right or left, the examiner can observe the eye with comfortable posture, facing straight to the biomicroscope, without shifting his position. In addition, the chin rest can be moved easily by the examiner or by the assistant.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A slit-lamp biomicroscope which illuminates an eye to be examined with slit illumination light, the biomicroscope comprising:

an illumination optical system provided with an illumination light source and a slit plate of which slit width is adjustable;

a plurality of types of filters each having a different optical characteristic which are inserted into, and removed from an optical path of the illumination optical system;

filter detection means for detecting a type of the filter being inserted in the optical path of the illumination optical system;

light amount change means for changing an amount of illumination light on a side of the illumination light source with respect to the slit plate; and control means for controlling the light amount change means such that the amount of illumination light is adjusted to an amount corresponding to the detected filter based on a detection result obtained by the filter detection means.

2. The slit-lamp biomicroscope according to claim 1, wherein the control means includes a memory for storing the amount of illumination light that corresponds to each filter.

3. The slit-lamp biomicroscope according to claim 1, further comprising slit width detection means for detecting the slit width, and wherein the control means includes a memory for storing the amount of illumination light that corresponds to each filter that in turn corresponds to an intended slit width.

4. The slit-lamp biomicroscope according to claim 1, further comprising slit width detection means for detecting the slit width, and wherein the control means includes:

a program for setting the amount of illumination light in correspondence to each filter that in turn corresponds to an intended slit width; and a memory for storing the amount of illumination light that is set through execution of the program.

5. The slit-lamp biomicroscope according to claim 4, further comprising a display for displaying information about the detected slit width and the amount of illumination light.

6. The slit-lamp biomicroscope according to claim 5, further comprising a photoelectric photographic optical system for photographing the eye, the photoelectric optical system also functions as an observation optical system, and
wherein the display further displays a photographed image of the eye.

7. The slit-lamp biomicroscope according to claim 1, further comprising:
operation means with which an operator manually adjusts the amount of illumination light; and
selection means for selecting whether to adjust the amount of illumination light manually or automatically by the control means.

8. The slit-lamp biomicroscope according to claim 7, wherein the selection means includes operation detection means for detecting whether or not the operation means has been operated.

9. The slit-lamp biomicroscope according to claim 1, further comprising:
slit width detection means for detecting the slit width;
signaling means for generating a signal for initiating control by the control means in case where the detected slit width is equal to a predetermined width or narrower.

10. The slit-lamp biomicroscope according to claim 1, further comprising:
a photoelectric photographic optical system for photographing the eye, the photoelectric optical system also functioning as an observation optical system; and
a display for displaying information about the amount of illumination light and a photographed image of the eye.

11. A slit-lamp biomicroscope which illuminates an eye to be examined with slit illumination light, the biomicroscope comprising:
an illumination optical system provided with an illumination light source and a slit plate of which slit width is adjustable;
a plurality of types of filters each having a different optical characteristic which are inserted into, and removed from an optical path of the illumination optical system;
filter detection means for detecting a type of the filter being inserted in the optical path of the illumination optical system;
slit width detection means for detecting the slit width;
a photoelectric photographic optical system for photographing the eye, the photoelectric optical system also functions as an observation optical system;
a display for displaying a photographed image of the eye as well as information about the detected slit width and the amount of illumination light;
light amount change means for changing an amount of illumination light on a side of the illumination light source with respect to the slit plate; and
control means for controlling the light amount change means such that the amount of illumination light is adjusted to an amount corresponding to the detected filter based on a detection result obtained by the filter detection means.

12. The slit-lamp biomicroscope according to claim 11, further comprising abase, and
wherein the display is supported by the base.

13. The slit-lamp biomicroscope according to claim 11, wherein the control means further controls the light amount change means such that the illumination light amount is adjusted to an amount corresponding to the detected slit width based on a detected result obtained by the slit width detection means.

14. A slit lamp biomioroscope, for illuminating an eye to be examined, comprising:
an illumination optical system provided with an illumination light source and a slit plate having an adjustable slit width;
slit width detection means for detecting the slit width;
light amount change means for changing an amount of illumination light on a side of the illumination light source with respect to the slit plate; and
control means for controlling the light amount change means such that the amount of illumination light is adjusted to an amount corresponding to the detected slit width based on a detection result obtained by the slit width detection means;
wherein the control means includes a memory for storing the illumination light amount that corresponds to an intended slit width.

15. A slit-lamp biomicroscope, for illuminating an eye to be examined comprising:
an illumination optical system provided with an illumination light source and a slit plate having an adjustable slit width;
slit width detection means for detecting the slit width;
light amount change means for changing an amount of illumination light on a side of the illumination light source with respect to the slit plate;
control means for controlling the light amount change means such that the amount of illumination light is adjusted to an amount corresponding to the detected slit width based on a detection result obtained by the slit width detection means; and
a display for displaying information about the detected slit width and the amount of illumination light.

16. The slit-lamp biomicroscope according to claim 15, further comprising a photoelectric photographic optical system for photographing the eye, the photoelectric optical system also functiond as an observation optical system, and
wherein the display further displays a photographed image of the eye.

17. A slit-lamp biomicroscope which illuminates an eye to be examined with slit illumination light, the biomicroscope comprising;
an illumination optical system provided with an illumination light source and a slit plate having an adjustable slit width;
slit width detection means for detecting the slit width;
light amount change means for changing a first amount of illumination light on a side of the illumination light source with respect to the slit plate; and
control means, having a program for setting a second amount of illumination light that corresponds to an intended slit width and a memory for storing the second amount of illumination light that is set through execution of the program, for controlling the light amount change means such that the first amount of illumination light is adjusted to the second amount of illumination light corresponding to the detected slit width based on a detection result obtained by the slit width detection means and the stored second amount of illumination light.

* * * * *

UNITED STATES PATENT AND TRADEMARK OFFICE
CERTIFICATE OF CORRECTION

PATENT NO. : 6,283,596 B1  Page 1 of 1
DATED : September 4, 2001
INVENTOR(S) : Kazuhiro Yoshimura et al.

It is certified that error appears in the above-identified patent and that said Letters Patent is hereby corrected as shown below:

Column 11, claim 12,
Line 64, "abase" should read -- a base --.

Column 12, claim 14,
Line 5, "biomioroscope" should read -- biomicroscope --.

Column 12, claim 16,
Line 42, "functiond" should read -- functions --.

Signed and Sealed this

Ninth Day of April, 2002

Attest:

JAMES E. ROGAN
Attesting Officer  Director of the United States Patent and Trademark Office